United States Patent
Li (10) Patent No.: US 9,224,188 B2
(45) Date of Patent: Dec. 29, 2015

(54) IMAGE PROCESSING DEVICE, METHOD AND PROGRAM

(75) Inventor: Yuanzhong Li, Kanagawa-ken (JP)

(73) Assignee: FUJIFILM CORPORATION, Tokyo (JP)

( * ) Notice: Subject to any disclaimer, the term of this patent is extended or adjusted under 35 U.S.C. 154(b) by 684 days.

(21) Appl. No.: 13/480,352

(22) Filed: May 24, 2012

(65) Prior Publication Data

US 2012/0306863 A1    Dec. 6, 2012

(30) Foreign Application Priority Data

May 30, 2011    (JP) .................................. 2011-120353

(51) Int. Cl.
G06T 3/00    (2006.01)
G06T 7/00    (2006.01)

(52) U.S. Cl.
CPC ............. *G06T 3/0068* (2013.01); *G06T 7/0024* (2013.01); *G06T 7/0028* (2013.01); *G06T 2207/10016* (2013.01); *G06T 2207/10081* (2013.01); *G06T 2207/10088* (2013.01); *G06T 2207/10132* (2013.01); *G06T 2207/10136* (2013.01); *G06T 2207/30048* (2013.01)

(58) Field of Classification Search
CPC combination set(s) only.
See application file for complete search history.

(56) References Cited

U.S. PATENT DOCUMENTS

| | | |
|---|---|---|
| 2003/0187350 A1 | 10/2003 | Omiya |
| 2007/0167806 A1* | 7/2007 | Wood et al. ................... 600/459 |
| 2008/0101532 A1* | 5/2008 | Tkaczyk et al. .................. 378/8 |
| 2009/0180675 A1* | 7/2009 | Li et al. ........................ 382/130 |
| 2010/0240996 A1* | 9/2010 | Ionasec et al. ................ 600/443 |
| 2010/0245360 A1* | 9/2010 | Song et al. .................... 345/441 |
| 2011/0208038 A1* | 8/2011 | Konofagou et al. .......... 600/410 |

FOREIGN PATENT DOCUMENTS

| | | |
|---|---|---|
| JP | 10-118061 A | 5/1998 |
| JP | 2003-79627 A | 3/2003 |

(Continued)

OTHER PUBLICATIONS

Duan, Qi, "Real-Time 4D Cardiac Image Analysis for Left Ventricular Function," PhD dissertation, Columbia University, 2008, 296 pages.*

R.I. Ionasec et al., "Patient-Specific Modeling and Quantification of the Aortic and Mitral Valves from 4-D Caridac CT and TEE", IEEE Transactions on Medical Imaging, vol. 29, No. 9, pp. 1636-1651, 2010.

(Continued)

*Primary Examiner* — Kee M Tung
*Assistant Examiner* — Roberta D Prendergast
(74) *Attorney, Agent, or Firm* — McGinn IP Law Group PLLC (57) ABSTRACT

A three-dimensional moving image and an ultrasonic moving image showing a body part making periodic motion are obtained, and, from the moving images, a characteristic part having a shape that changes with the periodic motion is extracted. Phases of the periodic motion captured in the moving images are obtained. For at least one of the moving images, the phases are obtained based on the shape of the extracted characteristic part. For each phase, the positions of the characteristic part shown in the three-dimensional moving image and the ultrasonic moving image are associated with each other based on the extracted characteristic part and the obtained phases. Comparison images are generated by aligning, for each phase, the positions of the characteristic part shown in the three-dimensional moving image and the ultrasonic moving image with each other based on the associated positions of the characteristic part and the phases, and displayed.

13 Claims, 3 Drawing Sheets

(56) References Cited

FOREIGN PATENT DOCUMENTS

| | | |
|---|---|---|
| JP | 2003-153877 A | 5/2003 |
| JP | 2003-290225 A | 10/2003 |
| JP | 2007-37781 A | 2/2007 |
| JP | 2009-022459 A | 2/2009 |
| JP | 2009-247739 A | 10/2009 |
| JP | 2010-29283 A | 2/2010 |

OTHER PUBLICATIONS

Y. Zheng et al., "Four-Chamber Heart Modeling and Automatic Segmentation for 3D Cardiac CT Volumes Using Marginal Space Learning and Steerable Features", IEEE Transactions on Medical Imaging, vol. 27, No. 11, pp. 1668-1681, 2008.

Notice of Grounds for Rejection dated Oct. 29, 2013, with English translation.

* cited by examiner

IMAGE PROCESSING DEVICE, METHOD AND PROGRAM

BACKGROUND OF THE INVENTION

1. Field of the Invention

The present invention relates to an image processing device, an image processing method and an image processing program for aligning and displaying a three-dimensional moving image taken with a CT or MR apparatus with a two-dimensional or three-dimensional moving image taken with an ultrasonic diagnostics apparatus.

2. Description of the Related Art

In the medical field, detailed three-dimensional moving images, which are obtained by imaging a body part of a patient making a predetermined periodic motion, such as the heart, with a modality having high spatial resolution and contrast resolution, such as a CT or MR apparatus, are widely used for imaging diagnosis.

On the other hand, ultrasonic moving images taken with an ultrasonic diagnostics apparatus, which has no problem of radiation exposure, etc., allows examination with a simple device, and provides information about blood flow based on reflection of ultrasonic waves by the blood flow, are also effective for imaging diagnosis. Further, along with the development of the ultrasound diagnostic technique, three-dimensional ultrasonic moving images of subjects have become available as the ultrasonic moving images, in addition to conventional ultrasonic moving images obtained with respect to a predetermined two-dimensional cross section of subjects.

In order to use advantages of both the above-described moving images, doctors conduct the imaging diagnosis with displaying both the moving images in a state where they show the same phase of heart beat based on electrocardiographic data that is obtained during imaging of each moving image. At this time, the user (doctor) references one of the images with manually changing the position and direction shown in the other of the images to be the same as those shown in the one of the images so that the moving images showing the same position and phase are displayed at the same time on a display in a manner allowing comparison therebetween. However, while a CT or MR image is taken in fixed position and orientation relative to the subject, an ultrasonic image is taken with pressing an ultrasound probe against the subject at an arbitrary angle. Therefore, it is difficult to identify the position and direction of the ultrasonic image relative to the subject. Further, it is necessary to identify a frame image forming the CT or MRI moving image and a frame image forming the ultrasonic moving image that correspond to the same phase. Therefore, it imposes significant time and labor on the user to display these moving images in a manner allowing comparison therebetween.

Japanese Unexamined Patent Publication No. 2003-153877 (hereinafter, Patent Document 1) has proposed a technique which involves: extracting a predetermined characteristic part, such as a blood vessel area including a blood flow image, from ultrasonic image data of an examined body part; aligning the position of the predetermined characteristic part shown in the ultrasonic image with the position of the predetermined characteristic part shown in an MR image obtained in advance; correcting the MR image such that the MR image and the ultrasonic image show the predetermined characteristic part in the same position; and superimposing the corrected MR image and the ultrasonic image and displaying the superimposed image on a display device.

Further, Japanese Unexamined Patent Publication No. 2009-022459 (hereinafter, Patent Document 2) has proposed a technique which involves: synchronizing timing of a three-dimensional CT moving image with timing of a three-dimensional ultrasonic moving image based on electrocardiographic data; reconstructing the ultrasonic image by transforming a spatial coordinate system of the ultrasonic moving image into a spatial coordinate system of the CT moving image using a transformation matrix; and displaying the reconstructed moving images being aligned and superimposed.

According to the technique taught in Patent Document 1, it is able to spatially align a three-dimensional still image taken with a CT apparatus with an ultrasonic still image. However, with the technique taught in Patent Document 1, a three-dimensional moving image taken with a CT apparatus and an ultrasonic moving image cannot be associated with the phases of heart beat, and therefore it is difficult to display the moving images such that they show the same phase and the same spatial position to allow comparison therebetween. Further, according to the technique taught in Patent Document 2, it is necessary to obtain electrocardiographic data corresponding to the moving images to align the moving images with each other with respect to the phase of heart beat. Therefore, in a case where the electrocardiographic data corresponding to one of or both of the moving images is not available, it is difficult to associate the corresponding phases of heart beat shown in the moving images with each other.

SUMMARY OF THE INVENTION

In view of the above-described circumstances, the present invention is directed to providing an image processing device, an image processing method and an image processing program that facilitate aligning a three-dimensional moving image taken with a CT or MR apparatus with an ultrasonic moving image with respect to phases of a periodic motion and the position thereof to generate and display comparison images of the three-dimensional moving image taken with a CT or MR apparatus and the ultrasonic moving image.

An aspect of the image processing device according to the invention is an image processing device including: image obtaining means for obtaining a three-dimensional moving image showing a body part of a patient and an ultrasonic moving image showing the body part, the body part making a predetermined periodic motion; characteristic part extracting means for extracting, from a plurality of frame images forming the obtained three-dimensional moving image and ultrasonic moving image, a predetermined characteristic part having a shape that changes in response to the periodic motion; phase obtaining means for obtaining phases of the periodic motion captured in the three-dimensional moving image and the ultrasonic moving image, wherein, for at least one of the three-dimensional moving image and the ultrasonic moving image, the phases are obtained based on the shape of the extracted characteristic part; associating means for associating, for each phase, a position of the characteristic part in a frame image forming the three-dimensional moving image corresponding to the phase with a position of the characteristic part in a frame image forming the ultrasonic moving image corresponding to the phase based on the extracted characteristic part and the obtained phases; image generating means for generating a comparison image of each of the three-dimensional moving image and the ultrasonic moving image by aligning, for each phase, a position of the characteristic part in a frame image forming the three-dimensional moving image corresponding to the phase with a position of the characteristic part in a frame image forming the ultrasonic moving image corresponding to the phase based on the associated positions of the characteristic part and the phases; and display controlling means for displaying the generated comparison images in a manner allowing comparison therebetween on a display device.

An aspect of the image processing method according to the invention is an image processing method including: obtaining a three-dimensional moving image showing a body part of a patient and an ultrasonic moving image showing the body part, the body part making a predetermined periodic motion; extracting, from a plurality of frame images forming the obtained three-dimensional moving image and ultrasonic moving image, a predetermined characteristic part having a shape that changes in response to the periodic motion; obtaining phases of the periodic motion captured in the three-dimensional moving image and the ultrasonic moving image, wherein, for at least one of the three-dimensional moving image and the ultrasonic moving image, the phases are obtained based on the shape of the extracted characteristic part; associating, for each phase, a position of the characteristic part in a frame image forming the three-dimensional moving image corresponding to the phase with a position of the characteristic part in a frame image forming the ultrasonic moving image corresponding to the phase based on the extracted characteristic part and the obtained phases; generating a comparison image of each of the three-dimensional moving image and the ultrasonic moving image by aligning, for each phase, a position of the characteristic part in a frame image forming the three-dimensional moving image corresponding to the phase with a position of the characteristic part in a frame image forming the ultrasonic moving image corresponding to the phase based on the associated positions of the characteristic part and the phases; and displaying the generated comparison images in a manner allowing comparison therebetween on a display device.

An aspect of the image processing program according to the invention is an image processing program for causing a computer to function as: image obtaining means for obtaining a three-dimensional moving image showing a body part of a patient and an ultrasonic moving image showing the body part, the body part making a predetermined periodic motion; characteristic part extracting means for extracting, from a plurality of frame images forming the obtained three-dimensional moving image and ultrasonic moving image, a predetermined characteristic part having a shape that changes in response to the periodic motion; phase obtaining means for obtaining phases of the periodic motion captured in the three-dimensional moving image and the ultrasonic moving image, wherein, for at least one of the three-dimensional moving image and the ultrasonic moving image, the phases are obtained based on the shape of the extracted characteristic part; associating means for associating, for each phase, a position of the characteristic part in a frame image forming the three-dimensional moving image corresponding to the phase with a position of the characteristic part in a frame image forming the ultrasonic moving image corresponding to the phase based on the extracted characteristic part and the obtained phases; image generating means for generating a comparison image of each of the three-dimensional moving image and the ultrasonic moving image by aligning, for each phase, a position of the characteristic part in a frame image forming the three-dimensional moving image corresponding to the phase with a position of the characteristic part in a frame image forming the ultrasonic moving image corresponding to the phase based on the associated positions of the characteristic part and the phases; and display controlling means for displaying the generated comparison images in a manner allowing comparison therebetween on a display device.

The "body part" herein may be any body part that makes a predetermined periodic motion, and a typical example thereof is the heart. The "predetermined periodic motion" herein may be any repeatable motion where each part included in the body part moves in a predetermined direction within a predetermined range, such as heart beat, respiration in lungs, flexion and extension of a joint, etc. Further, in the invention, in the case where the body part making the periodic motion is the heart, the characteristic part may be any of the ventricles, the atriums, the muscles, the valves and the apex of the heart. In this case, the phase obtaining means may obtain the phases based on a state of opening and closing of any of the valves of the heart. The phase obtaining means may optionally obtain the phases by identifying the end of diastole and/or systole of the heart based on the state of opening and closing of the mitral valve and/or the aortic valve among the valves of the heart.

In the invention, the three-dimensional moving image may be any three-dimensional moving image that shows the shape of a body part of a subject, and an example thereof is a three-dimensional moving image taken with a CT or MRI apparatus.

In the invention, the ultrasonic moving image may be a three-dimensional moving image or a moving image showing a cross section including the characteristic part.

The "phases of the periodic motion" herein refers to stages of the periodic motion, and the number of phases for one period of the periodic motion may be any number.

The description "displaying the generated comparison images in a manner allowing comparison therebetween on a display device" herein refers to any manner of display that allows comparison between the displayed comparison images. For example, the comparison images may be displayed side by side or in a column, or in a picture-in-picture format, where one of the comparison images is displayed in a small window on the other of the comparison images. Further, the comparison images may be displayed on a single display or on two or more displays. Still further, the comparison images may be displayed in the same size or in different sizes.

In the invention, the characteristic part extracting means may automatically extract the characteristic part.

In the invention, for at least one of the three-dimensional moving image and the ultrasonic moving image, the phase obtaining means may obtain the phases from accompanying information of the moving image.

In the invention, the image generating means may generate the comparison images by obtaining pixel spacing from accompanying information of each of the three-dimensional moving image and the ultrasonic moving image and providing the moving images with the same pixel spacing based on the obtained pixel spacing.

In the invention, the image generating means may generate, as the comparison image, the ultrasonic moving image shown by a color Doppler method based on Doppler shift of blood flow.

According to the image processing device, method and program of the invention, a three-dimensional moving image showing a body part, which makes a predetermined periodic motion, of a patient and an ultrasonic moving image showing the body part are obtained; from a plurality of frame images forming the obtained three-dimensional moving image and ultrasonic moving image, a predetermined characteristic part having a shape that changes in response to the periodic motion is extracted; phases of the periodic motion captured in each of the three-dimensional moving image and the ultrasonic moving image are obtained, wherein, for at least one of the three-dimensional moving image and the ultrasonic moving image, the phases are obtained based on the shape of the extracted characteristic part; for each phase, a position of the characteristic part in a frame image forming the three-dimensional moving image corresponding to the phase is associated with a position of the characteristic part in a frame image forming the ultrasonic moving image corresponding to the phase based on the extracted characteristic part and the obtained phases; a comparison image of each of the three-dimensional moving image and the ultrasonic moving image is generated by aligning, for each phase, a position of the characteristic part in a frame image forming the three-dimensional moving image corresponding to the phase with a position of the characteristic part in a frame image forming the ultrasonic moving image corresponding to the phase based on the associated positions of the characteristic part and the phases; and the generated comparison images are displayed on a display device. Therefore, even when there is no electrocardiographic data available, the comparison images of the three-dimensional moving image and the ultrasonic moving image can easily be generated based on the shape of the characteristic part. Further, the user can understand the object of observation at high spatial resolution by observing the comparison image generated based on of the three-dimensional moving image, and can easily understand the information that is obtained only from the ultrasonic moving image by observing the comparison image generated based on the ultrasonic moving image as necessary. This helps improving the efficiency and accuracy of diagnosis by doctors.

DESCRIPTION OF THE PREFERRED EMBODIMENTS

Hereinafter, embodiments of an image processing device, an image processing program and an image processing method of the present invention will be described in detail with reference to the drawings.

Figure 1:
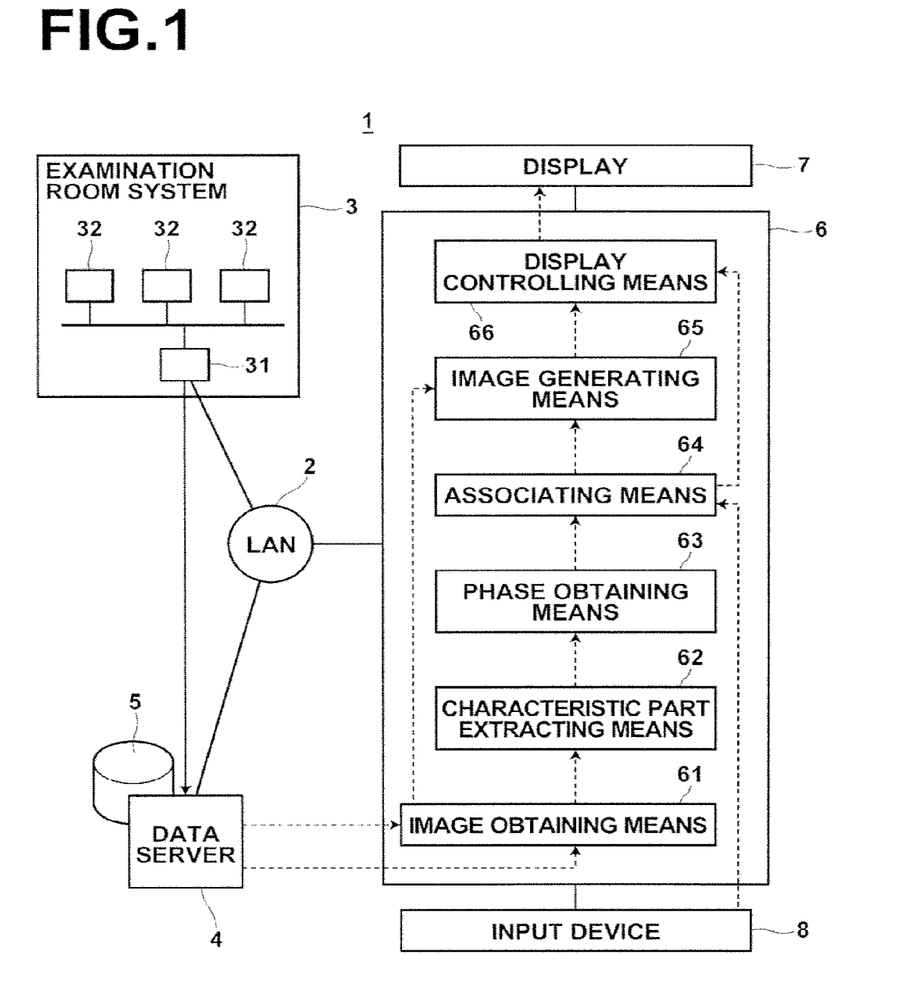
FIG. 1 is a diagram illustrating the schematic configuration of an image processing device according to one embodiment of the present invention.

FIG. 1 illustrates the schematic configuration of a hospital system 1 incorporating an image processing device 6 according to one embodiment of the invention. The hospital system 1 includes an examination room system 3, a data server 4 and a diagnosis workstation (WS) 6, which are connected with each other via a local area network (LAN) 2.

The examination room system 3 includes various modalities 32 for imaging a subject, and an examination room workstation (WS) 31 used for checking and controlling images outputted from the individual modalities. The modalities 32 in this example includes a CT (Computed Tomography) apparatus and an MRI (Magnetic Resonance Imaging) apparatus, which are able to obtain a shape image representing shape information of the heart, and also includes an ultrasonic diagnostics apparatus, etc. Among these modalities 32, the CT apparatus and the MRI apparatus are compliant to the DICOM (Digital Imaging and Communication in Medicine) standard, and output the obtained volume data as a DICOM file with adding accompanying information.

The file outputted from each modality 32 is transferred to the data server 4 by the examination room WS 31. The data server 4 is formed by a computer with relatively high processing capacity including a high-performance processor and a mass memory, on which a software program for providing the function of a database management system (DBMS) is implemented. The program is stored in a storage, loaded in the memory upon startup, and executed by the processor. The data server 4 causes the file transferred from the examination room WS 31 to be stored in a mass storage 5. Further, in response to a request to search from the diagnosis WS 6, the data server 4 selects a file that meets a search condition from files stored in the mass storage 5 and sends the file to the diagnosis WS 6.

The diagnosis WS 6 is formed by a general-purpose workstation including a standard type processor, a memory and a storage, on which the image processing program for assisting diagnosis is implemented. The image processing program is installed on the diagnosis WS 6 from a recording medium, such as a DVD, or downloaded from a server computer connected via the network before being installed. A display 7 and an input device 8, such as a mouse and a keyboard, are connected to the diagnosis WS 6.

The image processing program implemented on the diagnosis WS 6 is formed by sets of program modules for accomplishing various functions. Among them is a set of program modules for accomplishing the image processing function. The program is stored in the storage, loaded in the memory upon startup, and executed by the processor. With this, the diagnosis WS 6 operates as: image obtaining means 61 for obtaining a three-dimensional moving image V1 showing a body part (the heart), which makes a predetermined periodic motion, of a patient and an ultrasonic moving image V2 showing the body part; characteristic part extracting means 62 for extracting, from a plurality of frame images forming the obtained three-dimensional moving image V1 and ultrasonic moving image V2, a predetermined characteristic part (mitral valve MV) having a shape that changes in response to the periodic motion; phase obtaining means 63 for obtaining phases of the periodic motion captured in the three-dimensional moving image V1 and the ultrasonic moving image V2, wherein, for at least one of the three-dimensional moving image V1 and the ultrasonic moving image V2, the phases are obtained based on the shape of the extracted characteristic part; associating means for associating, for each phase, the position of the characteristic part in a frame image forming the three-dimensional moving image corresponding to the phase with the position of the characteristic part in a frame image forming the ultrasonic moving image corresponding to the phase based on the extracted characteristic part and the obtained phases; image generating means 65 for generating a comparison image I1, I2 of each of the three-dimensional moving image and the ultrasonic moving image by aligning, for each phase, the position of the characteristic part in a frame image forming the three-dimensional moving image V1 corresponding to the phase with the position of the characteristic part in a frame image forming the ultrasonic moving image V2 corresponding to the phase based on the associated positions of the characteristic part and the phases; and display controlling means 66 for displaying the generated comparison images I1 and I2 on the display device 7.

Figure 2:
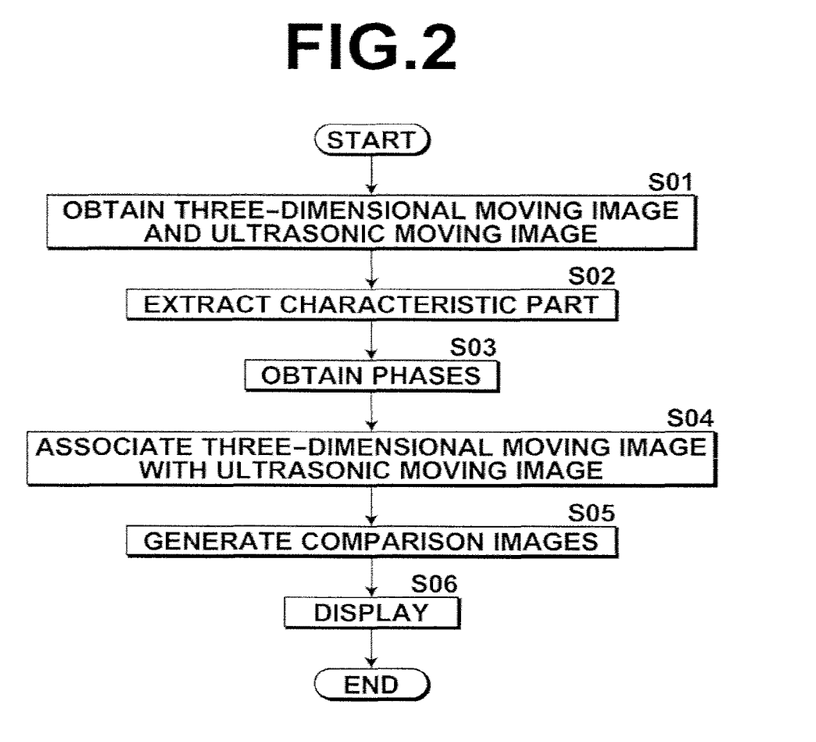
FIG. 2 is a diagram illustrating the flow of a process carried out by the image processing device according to one embodiment of the invention.
Figure 3:
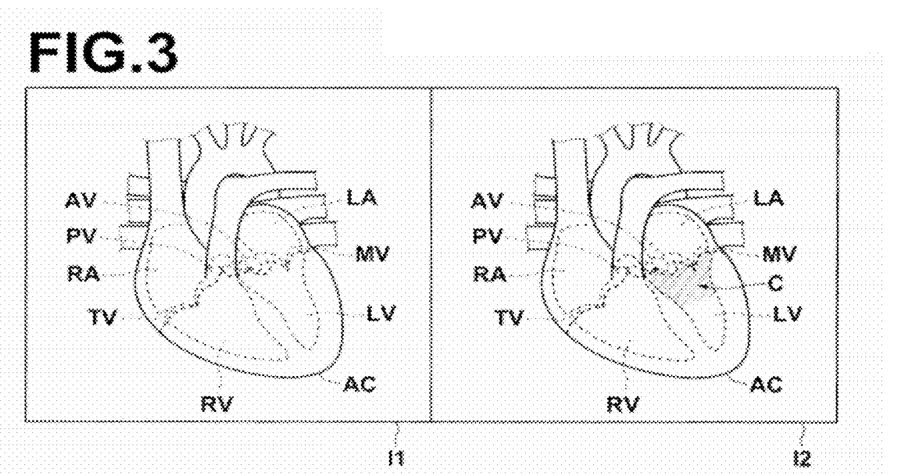
FIG. 3 is a diagram illustrating an example of comparison images displayed by the image processing device according to one embodiment of the invention.

FIG. 2 is a flowchart illustrating the flow of image processing of this embodiment. FIG. 3 shows an example of the displayed comparison images I1 and I2. Now, the flow of a process carried out by the functions of the WS 6 (image processing device) of this embodiment is described in detail using FIGS. 2 and 3. This embodiment is described in conjunction with the case of heart examination as an example.

Prior to the process of this embodiment, during the heart examination, a moving image of the chest of the subject including one period of heart beat is taken using a CT apparatus, or the like, and the thus taken three-dimensional moving image V1 (volume data) with the accompanying information added thereto is transferred as a DICOM file to the data server 4 and stored in the mass storage 5. The volume data is formed by a collection of pieces of voxel data representing a density distribution in a three-dimensional space. In each voxel data, X-ray absorption, or the like, is indicated as a voxel value. Further, a moving image of the chest of the same subject is taken by transesophageal echocardiography (TEE), which is ultrasound imaging carried out by inserting an ultrasound probe through the mouth to the esophagus, and the thus taken three-dimensional ultrasonic moving image V2 is transferred to the data server 4 and stored in the mass storage 5.

First, when an image processing function for the heart is selected on an initial screen and the patient ID number, the examination number, etc., are inputted on a predetermined input screen, the image obtaining means 61 sends the inputted information to the data server 4 and sends a request to search for and transfer the corresponding file stored in the mass storage 5.

The data server 4 which has received the above-described request searches for the requested file in the mass storage 5 and transfers the file to the image obtaining means 61. The image obtaining means 61 obtains the three-dimensional moving image V1 and the three-dimensional ultrasonic moving image V2 contained in the file transferred from the data server 4 and stores them in the memory (S01).

Subsequently, the characteristic part extracting means 62 extracts, as the predetermined characteristic part, the mitral valve MV, which is a heart valve located between the left ventricle LV and the left atrium LD, from each of the three-dimensional moving image V1 and the three-dimensional ultrasonic moving image V2 (S02).

In this example, the method taught in Razvan Ioan Ionasec, et al., "Patient-Specific Modeling and Quantification of the Aortic and Mitral Valves From 4-D Cardiac CT and TEE", IEEE Transactions on Medical Imaging, Vol. 29, No. 9, pp. 1636-1651, 2010, is applied to the operations to extract the characteristic part and obtain the phases from the three-dimensional moving image V1 and the three-dimensional ultrasonic moving image V2.

The characteristic part extracting means 62 segments the mitral valve MV of the heart captured in the moving images V1 and V2 in time series for at least one period of heart beat according to the method taught in the above-mentioned Non-Patent Document, and extracts information for identifying the position of each sample point on the contour of the mitral valve MV in each frame image forming the moving images V1 and V2.

Then, the phase obtaining means 63 obtains the phase of heart beat of each frame image based on the position of each sample point on the contour of the mitral valve MV captured in the moving images V1 and V2 (S03).

The one period of heart beat include a systole and a diastole. At the end of the systole, the aortic valve AV changes from the open state to the closed state and the mitral valve MV starts to open from the closed state. At the end of the diastole, the mitral valve MV changes to the closed state and the aortic valve starts to open from the closed state. Using this nature, the phase obtaining means 63 identifies the end of diastole and the end of systole to identify the phases of heart beat.

In this embodiment, the shape of the mitral valve MV captured in each of the moving images V1 and V2 is obtained at predetermined time intervals using predetermined parameters according to the method taught in the above-mentioned Non-Patent Document, and the state of opening and closing of the mitral valve MV is identified based on the shape of the mitral valve MV to obtain the phase of heart beat corresponding to the state of opening and closing of the mitral valve MV. In this embodiment, for each of the moving images V1 and V2, the state of opening and closing of the mitral valve MV and the predetermined parameters representing the shape of the mitral valve MV are associated with each other and stored. The phase obtaining means 63 identifies, for each moving image V1, V2, a frame in which the mitral valve MV has changed from the open state to the closed state as a frame corresponding to the end of diastole of the heart beat. Also, the phase obtaining means 63 identifies, for each moving image V1, V2, a frame in which the mitral valve MV has changed from the closed state to the open state (start-to-open state) as a frame corresponding to the end of systole of the heart beat. The predetermined parameters representing the shape of the mitral valve MV may, for example, be distances between specific sample points on the contour of the mitral valve MV.

Then, the associating means 64 temporally associates the frames forming the moving images V1 and V2 with each other such that the moving images V1 and V2 are aligned with each other with respect to the phases corresponding to the end of systole and the end of diastole (the associating means 64 may perform interpolation in the time axis direction, as necessary) (S04). In this example, the frame images of the images V1 and V2 showing the same phase are associated with each other, and the spatial position of the same characteristic part shown in the associated frame images is associated with each other.

In the above-described operation, in the case where the number of frames of the three-dimensional moving image V1 and the number of frames of the three-dimensional ultrasonic moving image V2 for one period differ from each other, the associating means 64 associates the frames of these images using the moving image having the smaller number of frames for one period as the reference. For example, the frames of the moving image having the greater number of frames for one period may be appropriately decimated, as necessary. Further, in the case where the phases of the associated frames are slightly out of alignment, interpolation may be performed using a known method so that each pair of corresponding frame images of the moving images shows the same phase. For example, the phase of each frame image forming one of the moving images may be obtained, and then, using frame images of the other of the moving images before and after the obtained phase, an interpolated frame image of the other of the moving images having the shape corresponding to the obtained phase may be generated by a known method, to associate the frame images of the one of the moving images with the thus generated frame images of the other of the moving images such that each pair of associated frame images shows the same phase.

The image generating means 65 generates volume rendered images for a series of frame images extracted from the three-dimensional moving image V1 by the above-described operation. For a series of frame images extracted from the three-dimensional ultrasonic moving image V2, the image generating means 65 generates images by transforming the coordinate system of the three-dimensional ultrasonic moving image V2 into the coordinate system of the three-dimensional moving image V1 so that the images V1 and V2 show the characteristic part associated by the associating means 64 in the same position, the same direction and the same size. Then, the image generating means 65 generates the comparison images I1 and I2 of the moving images V1 and V2 by a known method and stores the comparison images I1 and I2 in the storage 5 (S05).

Specifically, the image generating means 65 achieves the spatial alignment by transforming the coordinate system of one of the images into the coordinate system of the other of the images so that the images show the same characteristic part in the same spatial position based on the position associated by the associating means 64, and appropriately correcting the transformed coordinate system so that the images show the same characteristic part in the same spatial position, the same direction and the same size. It should be noted that, during the spatial position alignment, the associating means 64 obtains pixel spacing information of the three-dimensional moving image V1 and the three-dimensional ultrasonic moving image V2 from the DICOM header information of each image, and enlarges or reduces the moving images V1 and V2, as appropriate, based on the pixel spacing information to provide the series of frame images extracted from the three-dimensional moving image V1 and the three-dimensional ultrasonic moving image V2 with the same pixel spacing.

Further, as shown in FIG. 3, the comparison image I1 generated by the image generating means 65 of this embodiment shows voxel values based on the three-dimensional moving image V1 at a predetermined transparency by volume rendering, and as shown by arrow C in FIG. 3, the comparison image I2 generated by the image generating means 65 of this embodiment shows voxel values and the direction of blood flow based on the three-dimensional ultrasonic moving image V2 by the known color Doppler method.

As the method for generating the comparison images I1 and I2 of the series of frame images extracted from the three-dimensional moving image V1 and the three-dimensional ultrasonic moving image V2, the image generating means 65 may apply any of various known generation method that allows comparison between the displayed series of frame images extracted from the moving images V1 and V2 such that the comparison images I1 and I2 show the same characteristic part in the same spatial position, the same direction and the same size.

The display controlling means 66 obtains the comparison images I1 and I2 generated by the image generating means 65, and causes the display 7 to display the comparison images I1 and I2, as shown in FIG. 3 (S06).

As described above, according to this embodiment, the phases of the periodic motion of the body part that makes a predetermined motion are obtained based on the shape of the characteristic part captured in the three-dimensional moving image I1 and the ultrasonic moving image V2 and the three-dimensional moving image V1 and the ultrasonic moving image V2 are aligned with each other with respect to the phases to achieve the spatial alignment based on the position of the characteristic part captured in the moving images. Therefore, even in a case where the electrocardiographic data of one of the moving images is not available, the moving images can appropriately be associated with each other. Further, by displaying the comparison images I1 and I2 of the associated moving images in a manner allowing comparison therebetween, the user can understand the object of observation at high spatial resolution by observing the comparison image I1 based on the three-dimensional moving image V1, and can easily understand the information that is obtained only from the ultrasonic moving image by observing the comparison image I2 as necessary. Therefore, the user can efficiently and accurately conduct the imaging diagnosis. Still further, in this embodiment, the comparison images I1 and I2 of the moving images are displayed side by side in the same size. This facilitates the user to observe and compare the moving images with each other to understand the object of observation shown in the moving images even more easily and accurately.

In this embodiment, the comparison image I2, which is shown by the color Doppler method based on the Doppler shift of blood flow, is generated based on the ultrasonic moving image V2 and is displayed. Therefore, the user can preferably understand the blood flow information, which is obtained only from the ultrasonic moving image, from the comparison image I2 in an easy and intuitive manner.

In this embodiment, the shape of the characteristic part is automatically recognized to be extracted from the three-dimensional moving image V1 and the three-dimensional ultrasonic moving image V2 to eliminate the need of manual operation by the user to extract the characteristic part, and thus the shape of the characteristic part can be extracted efficiently and easily.

In the case where the body part that makes a periodic motion is the heart and the predetermined characteristic part is any of the valves of the heart, the periodic motion of the heart is accurately identified based on the state of opening and closing of the valves of the heart, thereby preferably obtaining the phases. Further, in this case, the phase obtaining means obtains the phases by identifying the end of diastole and/or systole of the heart based on the state of opening and closing of the mitral valve among the valves of the heart. Therefore, more accurate identification of the periodic motion of the heart is achieved based on the change of the shape of the characteristic part in response to the heart beat. Still further, in this embodiment, the associating means 64 aligns the moving images V1 and V2 with respect to the phases of heart beat (the end of systole and the end of diastole), thereby more accurately associating the moving images V1 and V2 with each other.

In this embodiment, the phases of both the three-dimensional moving image V1 and the ultrasonic moving image V2 are obtained by automatic recognition, and therefore the phases are easily and accurately obtained and associated. Alternatively, for one of the three-dimensional moving image and the three-dimensional ultrasonic moving image, the phases of the periodic motion may be identified based on the shape of the characteristic part, and for the other of the moving images, the phase of the periodic motion may be obtained based on the DICOM header information, or the like. In this case, the automatic recognition may be applied to only one of the moving images to minimize increase of computational load and efficiently obtain the phases of the moving images.

In this embodiment, the image generating means 65 generates the comparison images I1 and I2 by obtaining the pixel spacing from the accompanying information of each of the three-dimensional moving image V1 and the ultrasonic moving image V2, and providing the moving images with the same pixel spacing based on the obtained pixel spacing. This facilitates obtaining the pixel spacing of each moving image and accurately providing the moving images of the same size to generate the comparison images I1 and I2.

In this embodiment, the above-described image processing is carried out based on the three-dimensional moving image V1 taken with a CT or MR apparatus and the three-dimensional ultrasonic moving image V2, and this provides the user with more detailed understanding of the object of observation.

The characteristic part extracting operation according to this embodiment may be achieved by applying the method taught in Yefeng Zheng, et al., "Four-Chamber Heart Modeling and Automatic Segmentation for 3D Cardiac CT Volumes Using Marginal Space Learning and Steerable Features", IEEE Transactions on Medical Imaging, Vol. 27, No. 11, pp. 1668-1681, 2008. It should be noted that the characteristic part extracting means 62 may apply any of known various methods that can extract a characteristic part of a structure from the two three-dimensional moving images V1 and V2. For example, the user may manually input the position and shape of the characteristic part, such as the valves of the heart, using a mouse, or the like, for each of the three-dimensional moving images V1 and V2, and the image processing device may obtain such inputs to extract the position and the shape of the characteristic part.

The phase obtaining means 63 may determine the phases of heart beat by using any method that uses the nature that the aortic valve AV changes from the open state to the closed state and the mitral valve MV starts to open from the closed state at the end of systole, and the mitral valve MV changes to the closed state and the aortic valve starts to open from the closed state at the end of diastole. For example, a period from a point when the mitral valve MV starts to open from the closed state (the end of systole) to a point when the mitral valve MV again starts to open from the closed state (the end of systole) may be detected as the one period of heart beat to associate the images V1 and V2 such that the images are aligned with respect to the phase of the end of systole, or a period from a point when the mitral valve MV changes from the open state to the closed state (the end of diastole) to a point when the mitral valve MV again changes from the open state to the closed state (the end of diastole) may be detected as the one period of heart beat to associate the images V1 and V2 such that the images are aligned with respect to the phase of the end of diastole. Alternatively, for example, the phases of heart beat may be determined based on the state of opening and closing of the aortic valve AV, in place of the mitral valve MV, or information of the state of opening and closing of the mitral valve MV and information of the state of opening and closing of the aortic valve AV may be weighted to be used to determine the phase of heart beat.

In the case where any of various characteristic parts, such as the left ventricle LV, the left atrium LA, the right ventricle RV, the right atrium RA, the valves MV, AV, PV and TV and the apex AC of the heart, as shown in FIG. 3, or any combination of these characteristic parts is used as the predetermined characteristic part to identify the periodic motion of the heart based on the periodical change of the shape depending on the phase of heart beat, similarly to this embodiment, the phases are accurately obtained. In the case where more than one characteristic parts are used to identify the periodical motion of the heart, the phases are more accurately obtained based on the more than one pieces of information.

If the moving image V1 and/or the moving image V2 contains two or more periods of periodic motion, the phase obtaining means 63 may arbitrarily specify a period used to associate the moving images V1 and V2 with each other. The phase obtaining means 63 according to this embodiment receives an input by the user via a mouse and/or keyboard to identify one of the periods specified by the user by using any known method. For example, period selection buttons corresponding to the two or more periods contained in the three-dimensional moving image V1 or the three-dimensional ultrasonic moving image V2 may be displayed to receive the selection of period by the user, or the user may be prompted to input the start time of one of the periods contained in the three-dimensional moving image V1 or the three-dimensional ultrasonic moving image V2 via a keyboard, or the like, and the phase obtaining means 63 may receive the selection of period by the user.

Figure 4:
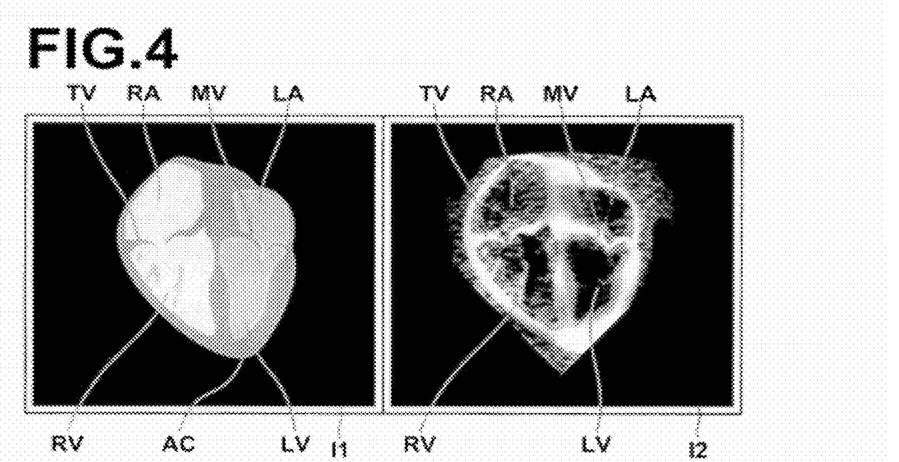
FIG. 4 is a diagram illustrating an example of comparison images displayed by a modification of the image processing device according to one embodiment of the invention.

FIG. 4 shows an example of the displayed comparison images I1 and I2 according to a modification of the above-described embodiment. Although the above-described embodiment is described in conjunction with the three-dimensional ultrasonic moving image V2 as an example, it is apparent for those skilled in the art that the invention is similarly applicable to a two-dimensional moving image taken with a ultrasonic diagnostic apparatus as long as the image shows a cross section showing a recognizable characteristic part included in a body part, such as a cross section P showing the ventricles LV and RV, the atriums LA and RA, the valves MV, AV, PV and TV and the apex AC of the heart, as shown in FIG. 4. The user can observe, with respect to a predetermined cross section including the characteristic part, a high spatial resolution image taken with a CT or MR apparatus, and can understand information, such as information of blood flow, which is obtained only from a two-dimensional moving image taken with an ultrasonic diagnostics apparatus at the same time. This facilitates the user to accurately conduct the imaging diagnosis.

It should be noted that the present invention is not limited to this embodiment. For example, the predetermined body part may be any body part that makes a predetermined periodical motion, such as flexion and extension of a knee joint. In the case where the invention is applied to flexion and extension of the knee, or the like, one or more parts forming the knee joint may be segmented to obtain parameters representing the state of flexion and extension of the knee, such as distances between predetermined points on the thigh bone and the shinbone, from the segmented parts, and the phases of the periodical motion from the flexed state to the extended state may be obtained based on the parameters representing the state of flexion and extension.

The display controlling means 66 may display the comparison images in any manner as long as the comparison images are displayed in a manner allowing comparison therebetween. For example, the comparison images may be displayed side by side or in a column, or in a picture-in-picture format, where one of the comparison images is displayed in a small window on the other of the comparison images. Further, the comparison images may be displayed on a single display or on two or more displays. Still further, the comparison images may be displayed in the same size or in different sizes. In the above-described embodiments, the comparison images I1 and I2 are displayed side by side in the same size. This facilitates doctors to compare the comparison images I1 and I2 with each other, thereby allowing efficiently and accurately conducting the imaging diagnosis.

It should be noted that the alignment of the three-dimensional moving image V1 taken with a CT or MR apparatus and the ultrasonic moving image V2 may be achieved by transforming the coordinate system of the three-dimensional moving image V1 taken with a CT or MR apparatus into the coordinate system of the ultrasonic moving image V2.

The associating means 64 may associate the phases of the three-dimensional moving image V1 taken with a CT or MR apparatus and the ultrasonic moving image V2 for only a part of one period of periodic motion, for one period of periodic motion, or for two or more periods of periodic motion.

Although the embodiments of the present invention have been described with respect to the case where the image processing program of the invention is implemented on a single diagnosis WS to cause the WS to function as the image processing device, the image processing program may be installed on two or more computers in a distributed manner to cause the two or more computers to function as the image processing device.

What is claimed is:

1. An image processing device comprising:
   an image obtaining unit for obtaining a three-dimensional moving image showing a body part of a patient and an ultrasonic moving image showing the body part, the body part making a predetermined periodic motion;
   a characteristic part extracting unit for extracting, from a plurality of frame images forming the obtained three-dimensional moving image and ultrasonic moving image, a predetermined characteristic part having a shape that changes in response to the periodic motion;
   a phase obtaining unit for obtaining phases of the periodic motion captured in the three-dimensional moving image and the ultrasonic moving image, wherein, for at least one of the three-dimensional moving image and the ultrasonic moving image, the phases are obtained based on the shape of the extracted characteristic part;
   an associating unit for associating, for each phase, a position of the characteristic part in a frame image forming the three-dimensional moving image corresponding to the phase with a position of the characteristic part in a frame image forming the ultrasonic moving image corresponding to the phase based on the extracted characteristic part and the obtained phases;
   an image generating unit for generating a comparison image of each of the three-dimensional moving image and the ultrasonic moving image by aligning, for each phase, a position of the characteristic part in a frame image forming the three-dimensional moving image corresponding to the phase with a position of the characteristic part in a frame image forming the ultrasonic moving image corresponding to the phase based on the associated positions of the characteristic part and the phases, the alignment is achieved by transforming the coordinate system of the three-dimensional moving image into the coordinate system of the ultrasonic moving image; and
   a display controlling unit for displaying the generated comparison images in a manner allowing comparison therebetween on a display device.

2. The image processing device as claimed in claim 1, wherein the characteristic part extracting unit automatically extracts the characteristic part.

3. The image processing device as claimed in claim 1, wherein the body part making the periodic motion comprises a heart, and the characteristic part comprises any of ventricles, atriums, muscles, valves and an apex of the heart.

4. The image processing device as claimed in claim 3, wherein the phase obtaining unit obtains the phases based on a state of opening and closing of any of the valves of the heart.

5. The image processing device as claimed in claim 4, wherein the phase obtaining unit obtains the phases by identifying an end of diastole and/or systole of the heart based on the state of opening and closing of a mitral valve and/or an aortic valve among the valves of the heart.

6. The image processing device as claimed in claim 1, wherein, for at least one of the three-dimensional moving image and the ultrasonic moving image, the phase obtaining unit obtains the phases from accompanying information of the moving image.

7. The image processing device as claimed in claim 1, wherein the image generating unit generates the comparison images by obtaining pixel spacing from accompanying information of each of the three-dimensional moving image and the ultrasonic moving image and providing the moving images with the same pixel spacing based on the obtained pixel spacing.

8. The image processing device as claimed in claim 1, wherein the image generating unit generates the comparison image shown by a color Doppler method based on Doppler shift of blood flow.

9. The image processing device as claimed in claim 1, wherein the ultrasonic moving image comprises a moving image showing a cross section including the characteristic part.

10. The image processing device as claimed in claim 1, wherein the three-dimensional moving image includes a plurality of axial sectional images, and
    wherein the ultrasonic moving image represents a sectional image in an angle and a position according to an angle and a position of an imaging probe.

11. The image processing device as claimed in claim 1, wherein the comparison image of the three-dimensional moving image is generated such that an angle and a position of the comparison image of the three-dimensional moving image are corresponding to an angle and a position of the comparison image of the moving ultrasonic image, for each phase.

12. An image processing method comprising:
    obtaining a three-dimensional moving image showing a body part of a patient and an ultrasonic moving image showing the body part, the body part making a predetermined periodic motion;
    extracting, from a plurality of frame images forming the obtained three-dimensional moving image and ultrasonic moving image, a predetermined characteristic part having a shape that changes in response to the periodic motion;
    obtaining phases of the periodic motion captured in the three-dimensional moving image and the ultrasonic moving image, wherein, for at least one of the three-dimensional moving image and the ultrasonic moving image, the phases are obtained based on the shape of the extracted characteristic part;
    associating, for each phase, a position of the characteristic part in a frame image forming the three-dimensional moving image corresponding to the phase with a position of the characteristic part in a frame image forming the ultrasonic moving image corresponding to the phase based on the extracted characteristic part and the obtained phases;
    generating a comparison image of each of the three-dimensional moving image and the ultrasonic moving image by aligning, for each phase, a position of the characteristic part in a frame image forming the three-dimensional moving image corresponding to the phase with a position of the characteristic part in a frame image forming the ultrasonic moving image corresponding to the phase based on the associated positions of the characteristic part and the phases, the alignment is achieved by transforming the coordinate system of the three-dimensional moving image into the coordinate system of the ultrasonic moving image; and
    displaying the generated comparison images in a manner allowing comparison therebetween on a display device.

13. A non-transitory storage medium containing an image processing program for causing a computer to function as:
- an image obtaining unit for obtaining a three-dimensional moving image showing a body part of a patient and an ultrasonic moving image showing the body part, the body part making a predetermined periodic motion;
- a characteristic part extracting unit for extracting, from a plurality of frame images forming the obtained three-dimensional moving image and ultrasonic moving image, a predetermined characteristic part having a shape that changes in response to the periodic motion;
- a phase obtaining unit for obtaining phases of the periodic motion captured in the three-dimensional moving image and the ultrasonic moving image, wherein, for at least one of the three-dimensional moving image and the ultrasonic moving image, the phases are obtained based on the shape of the extracted characteristic part;
- an associating unit for associating, for each phase, a position of the characteristic part in a frame image forming the three-dimensional moving image corresponding to the phase with a position of the characteristic part in a frame image forming the ultrasonic moving image corresponding to the phase based on the extracted characteristic part and the obtained phases;
- an image generating unit for generating a comparison image of each of the three-dimensional moving image and the ultrasonic moving image by aligning, for each phase, a position of the characteristic part in a frame image forming the three-dimensional moving image corresponding to the phase with a position of the characteristic part in a frame image forming the ultrasonic moving image corresponding to the phase based on the associated positions of the characteristic part and the phases, the alignment is achieved by transforming the coordinate system of the three-dimensional moving image into the coordinate system of the ultrasonic moving image; and
- a display controlling unit for displaying the generated comparison images in a manner allowing comparison therebetween on a display device.

* * * * *